(12) United States Patent
Wiest (10) Patent No.: US 8,212,158 B2
(45) Date of Patent: Jul. 3, 2012

(54) WEIGHT MEASURING SHOE HAVING A RETRACTABLE SCALE

(76) Inventor: Pieter C. Wiest, Detroit, MI (US)

( * ) Notice: Subject to any disclaimer, the term of this patent is extended or adjusted under 35 U.S.C. 154(b) by 331 days.

(21) Appl. No.: 12/422,388

(22) Filed: Apr. 13, 2009

(65) Prior Publication Data

US 2010/0258358 A1 Oct. 14, 2010

(51) Int. Cl.
*G01G 19/52* (2006.01)
*A43B 13/00* (2006.01)
*A43B 7/00* (2006.01)

(52) U.S. Cl. .............. 177/245; 36/136; 36/25 R; 73/172

(58) Field of Classification Search .................... 73/172, 73/379.01, 379.02; 340/666; 177/245; 36/136, 36/25 R
See application file for complete search history.

(56) References Cited

U.S. PATENT DOCUMENTS

| | | | | |
|---|---|---|---|---|
| 3,791,375 A | * | 2/1974 | Pfeiffer | 600/592 |
| 3,974,491 A | * | 8/1976 | Sipe | 340/573.1 |
| 4,465,294 A | | 8/1984 | Spitaler et al. | |
| 4,873,774 A | * | 10/1989 | Lafever | 36/61 |
| 5,253,654 A | * | 10/1993 | Thomas et al. | 600/592 |
| 5,269,081 A | * | 12/1993 | Gray | 36/136 |
| 5,333,892 A | | 8/1994 | Stritzl et al. | |
| 5,357,696 A | * | 10/1994 | Gray et al. | 36/136 |
| 5,456,027 A | * | 10/1995 | Tecchio et al. | 36/134 |
| 5,526,589 A | | 6/1996 | Jordan | |
| 5,655,316 A | * | 8/1997 | Huang | 36/132 |
| 5,673,500 A | * | 10/1997 | Huang | 36/136 |
| 5,732,482 A | * | 3/1998 | Remington et al. | 36/61 |
| 5,929,332 A | * | 7/1999 | Brown | 73/172 |
| 6,122,846 A | | 9/2000 | Gray et al. | |
| 6,590,166 B2 | * | 7/2003 | Yoshida | 177/25.13 |
| 6,629,698 B2 | * | 10/2003 | Chu | 280/11.19 |
| 6,718,200 B2 | * | 4/2004 | Marmaropoulos et al. | 600/547 |
| 6,807,869 B2 | * | 10/2004 | Farringdon et al. | 73/862.046 |
| 7,174,277 B2 | | 2/2007 | Vock et al. | |
| 7,234,250 B2 | | 6/2007 | Fogarty et al. | |
| 7,404,263 B2 | * | 7/2008 | Guzman | 36/133 |
| 7,607,243 B2 | * | 10/2009 | Berner et al. | 36/136 |
| 7,726,206 B2 | * | 6/2010 | Terrafranca et al. | 73/862.041 |
| 7,758,523 B2 | * | 7/2010 | Collings et al. | 600/592 |
| 8,015,732 B2 | * | 9/2011 | Berner et al. | 36/136 |
| 2002/0169387 A1 | * | 11/2002 | Marmaropoulos et al. | 600/547 |
| 2006/0230640 A1 | * | 10/2006 | Chen | 36/136 |
| 2006/0248965 A1 | * | 11/2006 | Wyatt et al. | 73/862.391 |
| 2007/0084642 A1 | * | 4/2007 | Maxi | 177/132 |
| 2010/0063778 A1 | * | 3/2010 | Schrock et al. | 702/188 |
| 2010/0211355 A1 | * | 8/2010 | Horst et al. | 702/173 |
| 2011/0214501 A1 | * | 9/2011 | Ross et al. | 73/172 |
| 2011/0314702 A1 | * | 12/2011 | Berner et al. | 36/136 |

FOREIGN PATENT DOCUMENTS

| | | | | |
|---|---|---|---|---|
| DE | 3937358 A1 | * | 5/1990 | 36/131 |
| JP | 54-115165 | * | 9/1979 | 177/245 |
| JP | 2005-214850 | * | 8/2005 | |

* cited by examiner

*Primary Examiner* — Randy W Gibson
(74) *Attorney, Agent, or Firm* — Young Basile Hanlon & MacFarlane PC (57) ABSTRACT

A shoe containing two scales entirely housed within its sole, which scales may be deployed downward so that they project beneath the shoe's sole—making the scales thereby able to accurately weigh the wearer as the wearer briefly stands only upon the thus deployed scales. After such a weight determination, the scales may be retracted—once again housed entirely within the shoe's sole—making the shoe ready to be worn and used in any and all conventional manners.

12 Claims, 6 Drawing Sheets

WEIGHT MEASURING SHOE HAVING A RETRACTABLE SCALE

FIELD OF THE INVENTION

This invention relates to at least one shoe of a pair of shoes, which shoe has at least one scale—and probably two scales—permanently attached to the shoe, and stored when not in use entirely within the sole-area of the shoe. When the scales are so stored (retracted) the shoe is suited for all uses to which shoes may be normally put. When the scales are deployed so as to cause a portion of the scales to project beneath the outer, lowest surface of the shoe's sole—the wearer, simply by standing on the so deployed scales, may quickly and easily ascertain her exact weight.

BACKGROUND OF THE INVENTION

The prior art shows a number of different types of footwear, for various purposes, having weight sensors—typically in the form of strain gages—adapted to provide a measurement of a person's weight or the distribution of weight over a footprint area or portion thereof. U.S. Pat. No. 7,174,277 to Vock et al. shows in FIGS. 57-62 a personal weighing system including a strain gage mounted in the tread or sole portion of a shoe and connected to a telemetry system for sending weight information to a remote receiver. (It should be noted re Vock et al. that the disclosures relative to the determination of an individual's weight are highly conceptual and some doubt obtains as to the ability of the systems and devices shown to accurately make the determination claimed. Specifically, determining the true weight of all object depends on the entire weight of the object being borne—supported—by the scale or scales alone. No portion of the object's weight may be borne or supported by anything other than the scale or scales. In the present invention, projecting the scale or scales beneath the shoe's sole insures that all of the subject's weight is borne and supported by the scale or scales alone.) Further prior art is shown in U.S. Pat. No. 6,122,846 to Grey et al., in which strain gages are mounted in a sensing unit in the sole of a shoe-type foot plate apparatus. This system is designed to communicate information to a remote display similar to that of Vock et al. A still further system is shown in U.S. Pat. No. 5,253,654 to Thomas et al. and includes a weight sensor disposed inside the shoe with a strain gage pad connected by a wire to a readout on the wearer's waist.

SUMMARY OF THE INVENTION

According to the present invention, one or more scales are permanently attached within tile sole of a shoe. When the scales are retracted—entirely stowed within the sole of the shoe—tile shoe may be used for all conventional purposes. As desired, however, the scales may be deployed. In the deployed position the bottom-most portion of the scales project beneath the sole of the shoe. By standing briefly on one foot—that with the shoe containing the scales, now deployed—the wearer may weigh himself.

In the preferred embodiment, the present invention uses two scales, rectangular in shape, integrated within the sole of one of the shoes. A description of one of these scales will be understood to act as a description of both scales, which are identical. The scale in the invention being described consists of two main rectangular structural pieces. The top of the upper rectangular structural piece is attached to the shoe within the shoe's sole area. (Note that a wide array of sole designs may be found fitting for the implementation of the invention, including those with integrated horizontal and/or vertical support elements disposed throughout the sole when and as necessary.) The upper rectangular structural piece has a large spring within it. This spring can be contracted or allowed to expand. Because it bears on the top of the lower rectangular structural piece, when it expands it causes this lower piece—which has, heretofore, been nestled within the slightly larger upper piece—to be projected downward. When the lower piece of the scale is thus deployed—projecting approximately 3/16" beneath tile ground line of the shoe's sole, that is, the sole's bottom-most point—the wearer's weight, when standing on the scale, causes deformation to take place in a strain gage which is embedded within the lower structural piece of the scale. This allows an accurate determination to be made of the wearer's weight. This weight determination may then be made available to the wearer by various means.

When the lower structural piece is retracted within the upper structural piece, the lower piece is held in the retracted configuration by locks. This insures that the wearer may utilize the shoes in all conventional ways, as the scale is completely retracted within the shoe. When the lower structural piece is deployed, another set of locks holds this piece in this deployed configuration. This configuration, and these locks, allow the wearer, standing on the deployed scale, to determine her weight. Upon completion of the weighing function, the set of locks which keep the scale deployed are released allowing the user to retract—by placing her weight upon the scale—the lower piece of the scale upward into the upper piece of the scale. This retraction contracts the large spring once again and additionally causes the locks which hold the lower piece nestled within the upper piece to re-engage. These locks are selectively activated to facilitate deployment or retraction by a push button, a sensor, and electromagnets, all of which are part of an electronic circuit that also includes the necessary means of weight determination—the strain gage—as well as a microprocessor and a battery.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views and wherein:

FIG. 1 is a side view of an athletic shoe modified by the addition of two scales. (Portions of the shoe not material to the invention have been removed in this and the following two illustrations.) This depiction of the preferred embodiment of the invention is seen with the scales retracted. (Also, in the depiction of the front scale in FIGS. 1 and 2, the entire side panel of the upper structural piece—the side facing the viewer of this rectangularly-shaped cubic structural piece—has been removed to make possible a visualization of the construction of the scale's upper and lower structural pieces, and the lower structural piece's locks and electromagnets. The scale's sensor may also be seen. Also shown is tile large spring, the box-shaped cutout which accommodates it, and the strain gage. Also, in FIGS. 1 and 2, the side panel of the upper structural piece of the rear scale has been left in place. Additional structural aspects of the invention, and the locks, electromagnets, sensor, large spring, and strain gage are further illustrated and discussed hereinafter.);

FIG. 6B is drawn as on the center line of FIGS. 6A and 6C;

DETAILED DESCRIPTION OF AN ILLUSTRATIVE EMBODIMENT

A portion of the disclosure of this patent document contains material which is subject to copyright protection. The copyright owner has no objection to facsimile reproduction, by anyone, of the patent document or the patent disclosure as it appears in the Patent and Trademark Office patent file or records, but otherwise reserves all copyright rights whatsoever.

Figure 1:
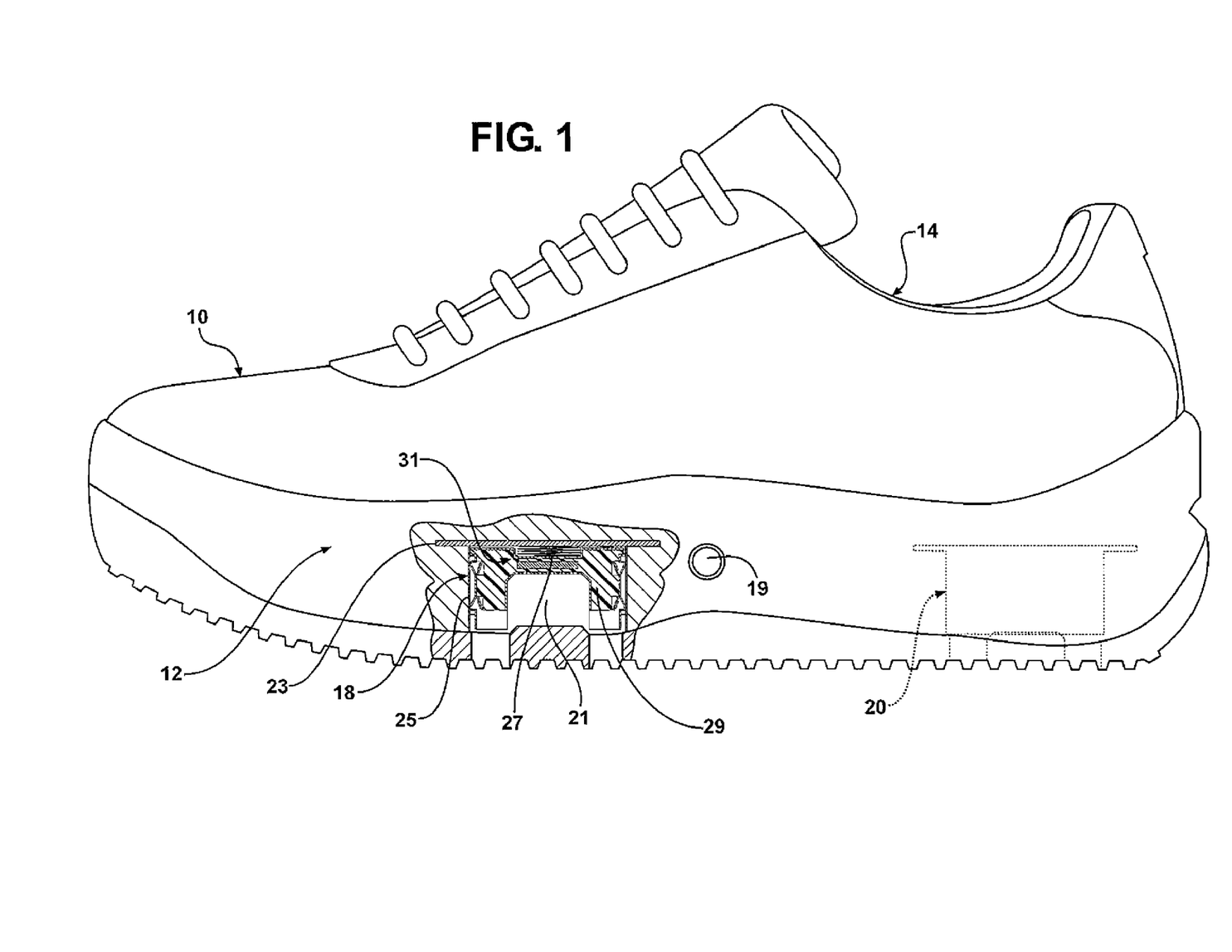

Referring first to FIG. 1, there is a shoe 10, which type of shoe depicted is merely illustrative, having a sole 12, an upper 14, two scales 18, 20 and a push button 19.

FIG. 1 shows the two scales, as described in the Brief Description Of The Drawings, permanently attached within the sole 12 of the shoe 10. Hereinafter, it will be appreciated that only one scale—the front scale 18—is being described, as the two scales are, in actual use, identical with the exception of the orientation of the strain gage in the rear scale—as explained below in the discussion of FIG. 3.

The shoe's sole-materials surround and are contiguous with the top plate and the upper structural piece of the scale. Beneath this piece of the scale, an enclosed cavity 21 exists within the sole to accept the downward deployment of the scale's lower structural piece. Further, vertical slots extend downward from the bottom of this cavity to the bottom edge of the sole. Thus the scale may be entirely retracted, that is, contained within the shoe—and yet may also be deployed, causing a portion of the scale to project beneath the bottom of the shoe. As shown, the two scales are in their retracted position.

The top-most element of the scale is a top plate 23 embedded within the sole of the shoe. This plate is comprised of a composite material formulated to be appropriately resistant to excessive flexion while still retaining modest flexibility. Immediately beneath, and attached to this top plate, is the upper structural piece 25 of the scale. This upper structural piece is, in its simplest form, a hollow rectangular shape consisting of four sides. Its top is the aforementioned top plate. It has no bottom surface so as to allow for the inclusion of the lower structural piece within it when the lower structural piece is retracted. Also attached to the top plate, and centrally positioned relative lo tile upper structural piece, is a large spring 27. This spring, shown retracted, bears on the top of the lower structural piece 29 of the scale 18. As with the upper structural piece, the lower structural piece has four sides. It also has a top surface. This top surface is relatively thick and contains as an aspect of its design the box-shaped cutout 31—a depression centered on the top surface of the lower structural piece. The top of this lower structural piece also contains within its thickness the strain gage (indicated with diagonal hatching). In the view being discussed both the box-shaped cutout and the strain gage would not be visible; however, they are shown here to indicate their inclusion at the center—top to bottom and side to side—of the top portion of the lower structural piece. (Neither the box-shaped cutout or the strain gage reach any of the four edges of the top section of the lower structural piece.) In addition to the thick top portion of the lower structural piece, the lower structural piece also has four descending legs which are L-shaped in section. Note that the aforementioned box-shaped cutout allows for an efficient storing of the large spring when tile scale is in its retracted position, as shown here. The lower structural piece 29 of the scale is housed within the upper structural piece 25, as shown, when tile scale is in its retracted position.

In FIG. 1 we note, as part of the lower structural piece 29—of the scale 18—two upper locks, two upper electromagnets, two lower locks, two lower electromagnets, a sensor, and a strain gage. These elements are hereinafter described in detail. It should also be noted in FIG. 1 that when the lower structural pieces of the scales are thus retracted—entirely stowed within the sole of the shoe—the shoe is in readiness for all conventional uses.

Figure 2:
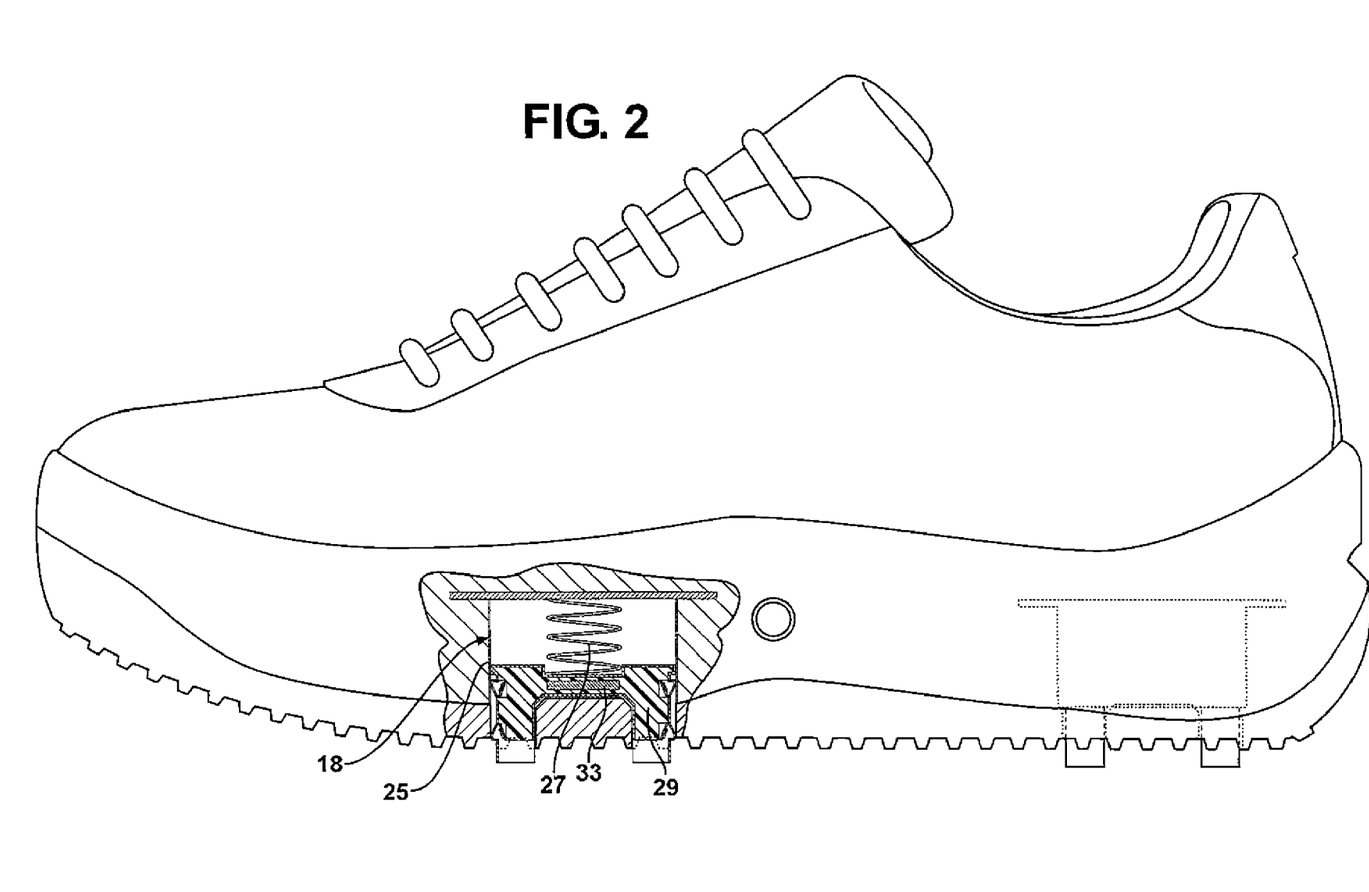
FIG. 2 is a side view of the same shoe as above in which may be seen the scales as they are when deployed. The push button may also be seen on the side of the shoe.

Looking at FIG. 2 we see that the large spring 27 expands within the front scale 18. Due to the large spring's bearing on the top of the lower rectangular structural piece 29, this lower piece, which has heretofore been nestled within the slightly larger upper structural piece 25, is caused to be projected downward. When the lower structural piece of the scale is thus deployed—its lowest part projecting approximately 3/16" beneath the ground line of the shoe's sole, that is, the sole's bottom-most point—a wearer's weight, bearing on the scale, causes specifically-measurable deformation to take place in the strain gage 33a/33b, which is embedded within the lower structural piece 29 of the scale 18. Note that this strain gage's long axis aligns with the long axis of the wearer's foot.

Figure 3:
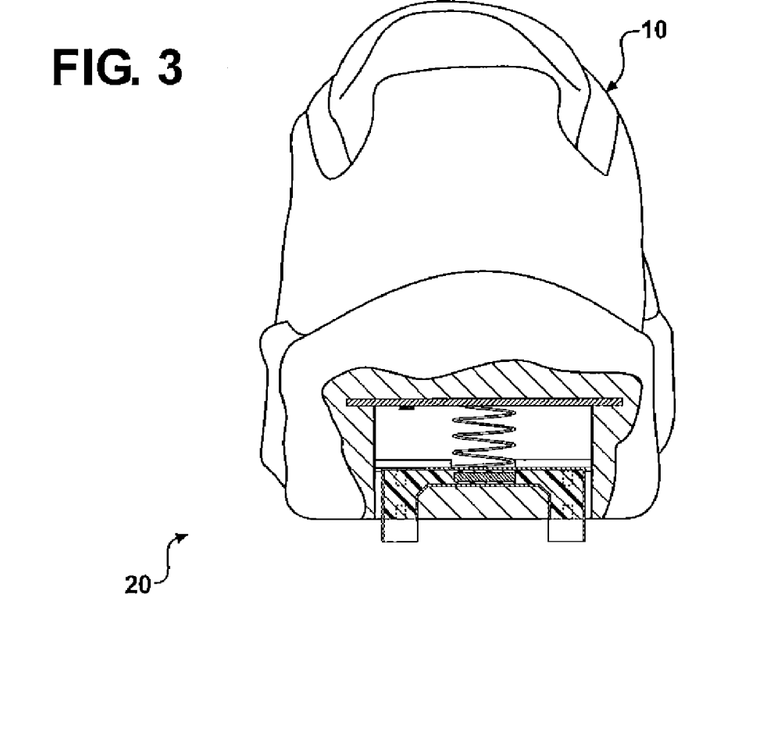
FIG. 3 is an end view of the above shoe in which may be seen the rear scale as it is when deployed; (Note that the end panel of the upper structural piece has been removed.)

In FIG. 3 we see the placement of the rear scale 20 relative to the width of the shoe 10. The long axis of the strain gage (indicated with diagonal hatching) in this, the rear scale, aligns with the short axis of the wearer's foot. Note: This is the only difference between the front scale and the rear scale.

Figure 4:
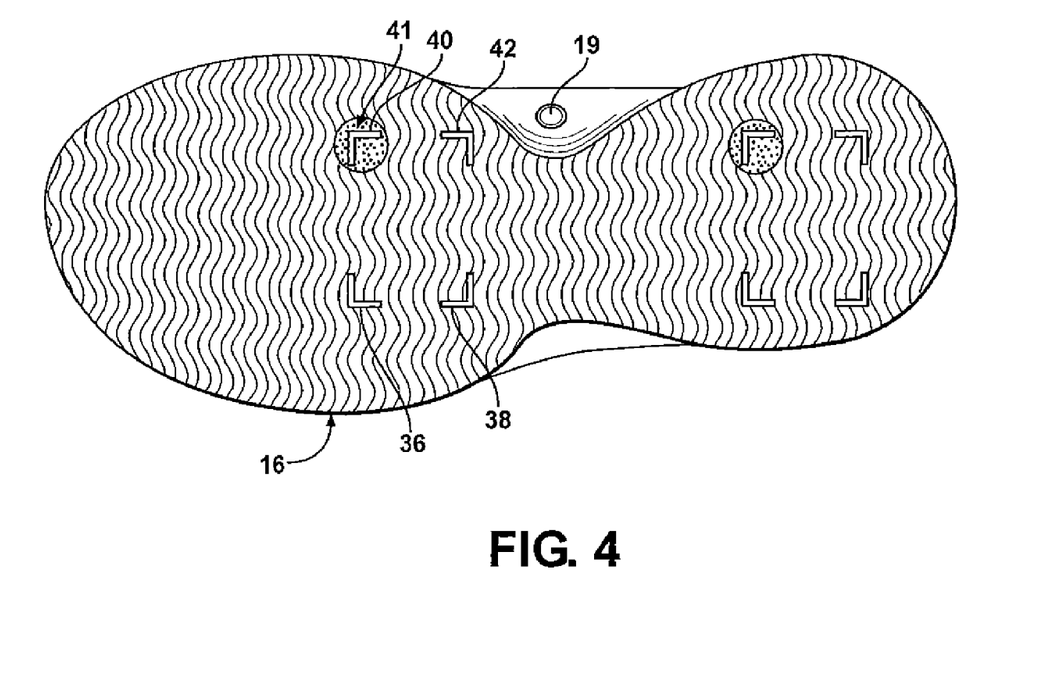
FIG. 4 is a bottom view of the above shoe's sole, and tread, in which the scales are retracted; in this view may be seen the apertures through which the portion of the scales that engage the ground are deployed. Also seen are the circular concavities for use in retraction of the scales; these are discussed more fully hereinafter. The push button, a part of the electronic circuitry, is also shown.

FIG. 4 is a view of the sole 16 in which both scales are retracted. Speaking to those features pertaining to the front scale only, we see apertures 36, 38, 40, 42 through which a portion of the scale's lower structural pieces descend when deployed. Also visible is the circular concavity 41 that facilitates the retraction of the scale. This concavity, and the push button 19 used in retraction and deployment of the scale, are described hereinafter.

Figure 5A:
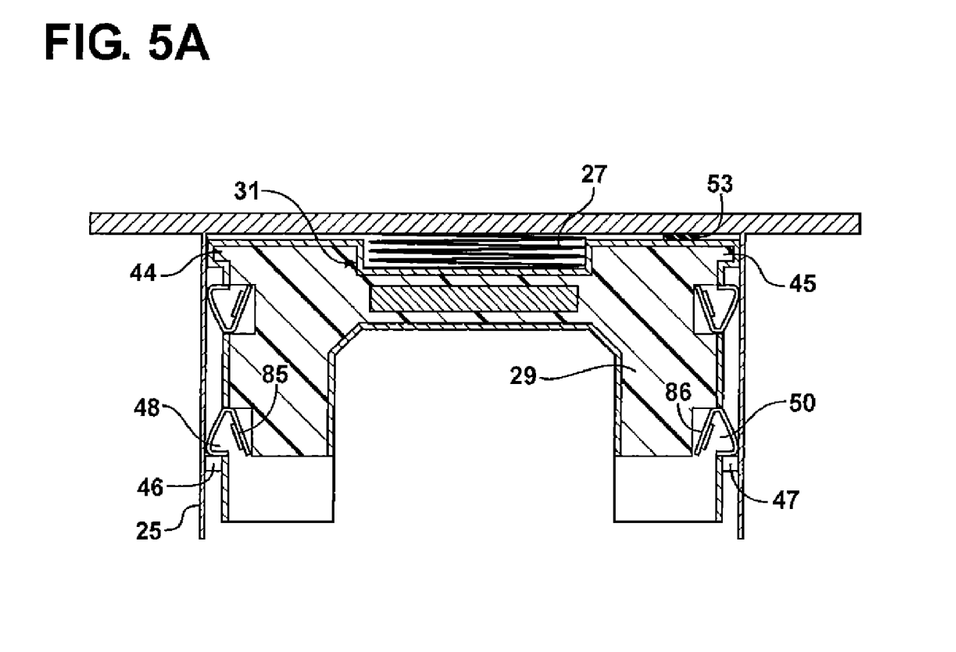
FIG. 5A is a detailed drawing of the flanges, locks, and electromagnets of two arrays—there being four such arrays, all identical in construction—on each of the two scales. This drawing depicts the scale as retracted. The sensor and strain gage may also be seen. (Additionally, note that the side panel of the upper structural piece has been removed in this illustration and that which follows.)

In FIG. 5A (this drawing and the one that follows have the side panel of the upper structural piece removed; see Brief Description Of The Drawings) we see a detailed drawing that illustrates, in simplified form, the manner in which the scale's retraction is maintained. The locks and the electromagnets, herein shown and described at only two corners of the rectangular lower structural piece, occur in like fashion at a position near each of the four corners of the rectangular lower structural piece. Further, the two lower structural piece flanges 44, 45, and the two upper structural piece flanges 46, 47, which aid in securing the scale in its two modes, run the entire length of the sides of the respective rectangular structural pieces on which they are found.

Looking first at the lower structural piece 29, we see that it is retracted, that is, nestled within the upper structural piece 25. It is held thus by the lower steel cam locks 48, 50 which locks bear downward on the upper structural-piece flanges 46, 47 (parts of the upper structural piece 25). We also see the sensor 53, the large spring 27 that bears on the top of the lower structural piece 29, and the box-shaped cutout 31 in the center of the top of this piece—which cutout houses the spring. Additionally, the strain gage is evident situated in the lower structural piece. It should be noted here that the two steel cam locks 48, 50 are—as are all of the scale's cam locks—supplied with a constant outward-bearing bias by the presence of a small helical spring that is an aspect of their design. (The inward withdrawal of these two locks 48, 50 is affected when called for—as in the scale's deployment—by the activation of the two appropriate lower electromagnets 85, 86.) The design of the steel cam locks and their function, and the function of the electromagnets and of the sensor are hereinafter more fully described.

When the lower structural piece is retracted within the upper structural piece, and the spring in the upper piece bearing on the top of the lower piece is contracted—the lower piece thus held in the retracted configuration by locks—the wearer may utilize the shoe in any desired conventional manner.

Figure 5B:
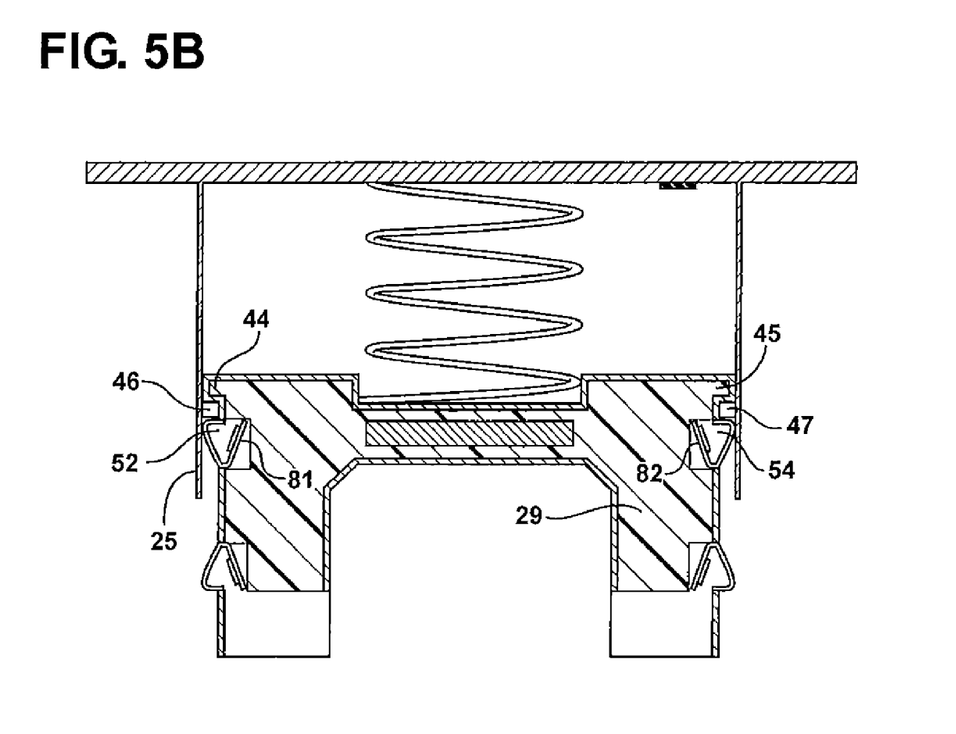
FIG. 5B is a detailed drawing similar to that above, however, herein the scale is deployed.

FIG. 5B shows the lower structural piece 29 deployed. In this configuration the shoe is ready to electronically render the weight of its wearer. The detailed drawing here shows that, having been deployed, the lower structural piece's upper steel cam locks 52, 54 bear their respective portion of the wearer's weight by their support of the upper structural-piece flanges 46, 47 upon which the wearer's weight rests. The lower structural-piece flanges 44, 45 (parts of the lower structural piece 29) help to reinforce the stability of the lower structural piece, when deployed, by their contiguity with the upper structural-piece flanges 46, 47. Further stability of the scale is gained by a partial overlapping on all four sides of the lower structural piece 29 by the four side panels of the upper structural piece 25. (Note that when the upper steel cam locks 52, 54 need to be inwardly withdrawn—as for the scale's retraction—it is done by activation of the two upper electromagnets 81, 82.) As in FIG. 5A, the locks and the electromagnets, herein shown and described at only two corners of the rectangular lower structural piece, occur in like fashion at a position near each of the four corners of the rectangular lower structural piece.

Figure 6A:
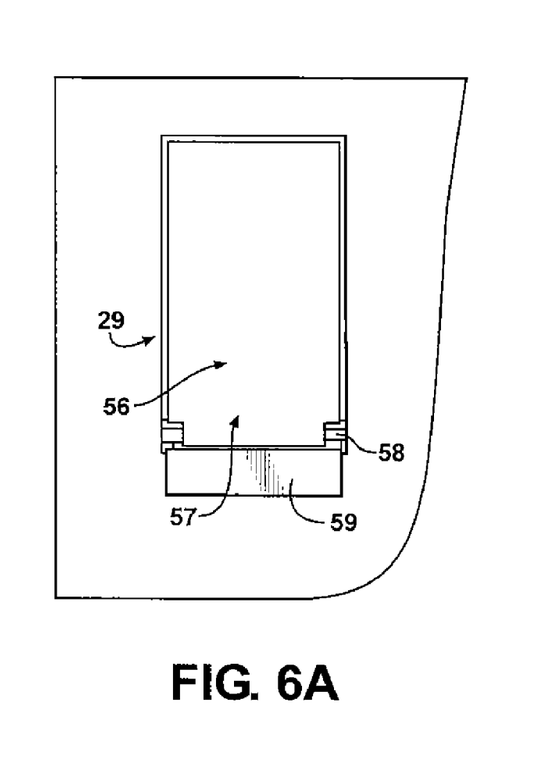
FIGS. 6A, 6B, and 6C are detailed drawings of the steel cam locks. As pictured they represent upper cam locks. The lower cam locks are identical except for a 180-degree rotation, spatially.

FIG. 6A is a detailed drawing giving a front view of one of the cam locks. It is suggested that these locks may be made of a thin ferromagnetic metal, such as steel, which has high structural strength. The main parts of the steel cam lock, as seen here, are the steel cam itself 56 and the base portion 57—both of which are integral parts of the cam lock. This base portion 57 curls around and up, creating a central horizontal tunnel. (For this, and the immediate following, see FIGS. 6B and 6C.) The steel axle 58 runs through this tunnel. The cam lock is held in its outward-bearing attitude by a small spring that surrounds, helically, the axle and extends along the long axis of the axle. The small spring is thus housed in such a way as to be wrapped around the axle 58 and stored within the tunnel.

Further regarding FIG. 6A, around the lower edge of the opening in the lower structural piece 29, in which the cam lock operates, we see a steel reinforcing piece 59. As drawn, this piece lies flat on the front surface of the lower structural piece, and wraps over the bottom edge of the opening in which the steel cam lock operates.

Figure 6B:
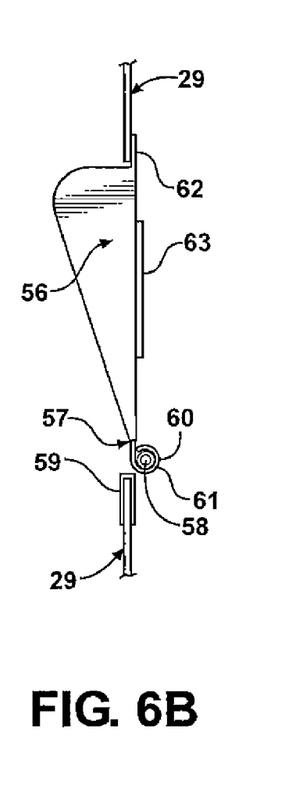

FIG. 6B shows one of the steel cam locks in side view (as on the center line of FIGS. 6A and 6B). We see the central horizontal tunnel 60, the small spring 61 within the central horizontal tunnel, and the steel axle 58 within the small spring. The cam lock's steel retaining flange 62 is also seen. It should be noted that this flange 62 along with the cam portion 56 and the base portion 57 are all integral parts of the steel cam lock. We also note the brace 63 and reinforcing piece 59.

Figure 6C:
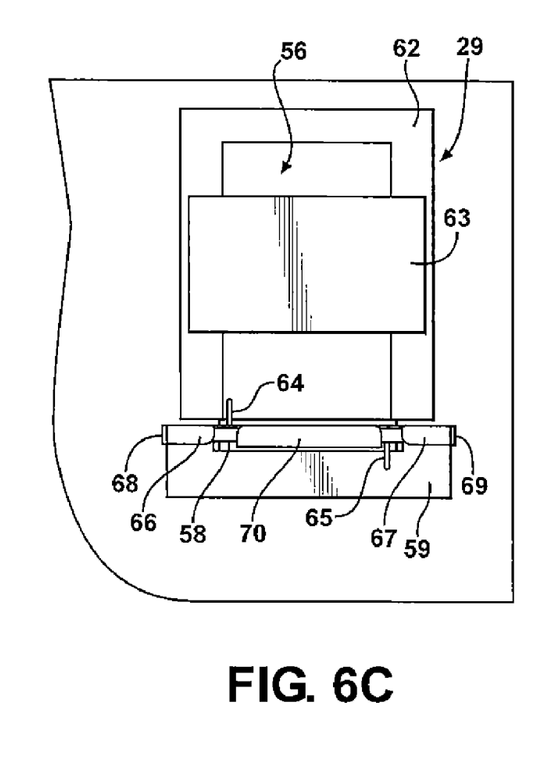

FIG. 6C shows the back of one of the steel cam locks. We note the back of the main part of the forward-protruding cam lock—the cam itself 56. We also see the steel axle 58 and the ends 64, 65 of the small spring. Further note the cam lock's steel retaining flange 62, as earlier noted, an integral part—along with the cam portion and the base portion—of the cam lock. This retaining flange, in addition to properly restraining the lock's outward travel, gives stability to the lock and the surrounding lower structural piece of the scale. Additionally, there is a brace 63 which spans the breadth of the back of the cam lock. This brace not only stabilizes the lock, it also provides an appropriately placed ferromagnetic surface to bring about an effective electromagnetically-induced inward withdrawal of the lock. The small spring is of a length that is almost equal to the width of the front of the cam lock. We see that this small spring has one end 65 that deploys downward and lies, as a result of its inherent bias, along the back of the rear surface of the reinforcing piece 59. The other end 64 of this spring deploys upward and lies, also with the pressure of inherent bias, along the back of the cam lock.

As in the above two drawings, we also see the reinforcing piece 59. This piece, as shown, wraps over the bottom edge of the opening in which the steel cam lock operates. However, this reinforcing piece 59 extends farther outward to the left- and right-hand sides on this, the back side of the lower structural piece 29, than it does on the front of the lower structural piece. This allows for the steel of the reinforcing piece 59 to be formed into two lateral horizontal tunnels 66, 67—each housing one end of the steel axle 58—which help hold the axle in place. Additionally, steel tabs 68, 69 are part of the reinforcing piece 59. These tabs, when folded over the ends of the two lateral horizontal tunnels 66, 67, secure the axle 58. We also see here the central horizontal tunnel 70, which further helps to hold the axle 58 in place.

Figure 7:
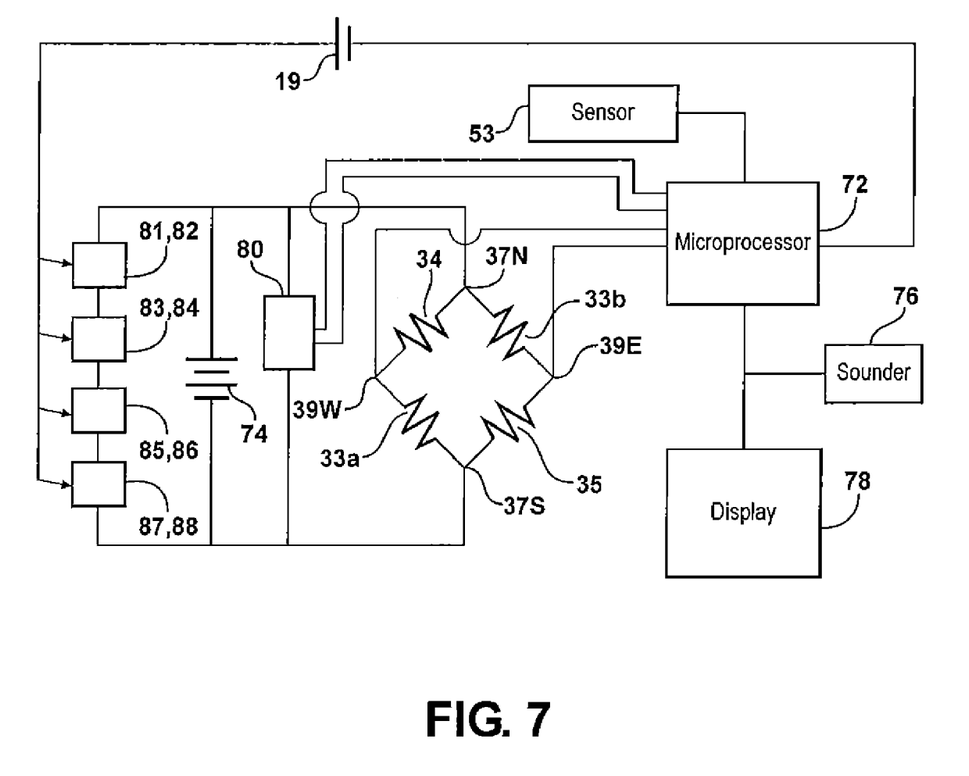
FIG. 7 is a schematic diagram of the electronic circuitry of the illustrated embodiment.

FIG. 7 is a schematic diagram of an electronic circuit suitable to the invention as described. (As per the above descriptions wherein only one scale is discussed in detail, this schematic shows only one Wheatstone bridge and eight electromagnets—the number necessary for the proper functioning of one scale.) The electronic circuit is embedded within the lower portion of the shoe, probably within the area of the sole. It includes a microprocessor 72. This device is connected to two nodes of a conventional Wheatstone bridge that uses as opposite variable-resistor legs the strain gage 33a/33b, indicated by arrows through the resistor symbols. Fixed-resistors 34, 35 comprise the other two legs, and the opposite or north/south nodes 37N, 37S are connected across a battery 74. The weight-related information, necessary for an accurate weight determination by the microprocessor, is taken across the east/west nodes 39E, 39W of the Wheatstone bridge. When this has been completed, the sounder 76 produces an audible tone, indicating to the wearer that an accurate weight signal has been obtained. Through speech-simulation, the sounder 76 may be utilized to announce this weight information. Additionally or alternatively, this weight information may be transmitted by means of the electronic circuit's display function 78 to a device mounted somewhere on the shoe—perhaps a small display screen that can be affixed by means of the shoe's laces. (This small, accessory-type, display-screen device is not shown in the drawings of the shoe.)

Additionally or alternatively, the invention's implementation may include the weight information being transmitted by a radio-frequency telemetry device 80, a part of the shoe's electronic circuit, to any remote electronic device capable of receiving such transmissions for visual and or acoustic display. Through such radio-frequency transmission, computers, iPods, MP3 players, Blackberrys, cell phones, iPhones, Instant Messaging machines, watches, pagers, digital storage devices, and devices worn on the belt, arm, or wrist, etc., may receive, store, and retrieve the wearer's weight information. (Also note that some methods of sending weight information to a remote location are described in the prior art of the Vock et al., and the Grey et al. patents.)

The microprocessor 72 is also connected through the push button 19, to the eight electromagnets—four upper electromagnets 81, 82, 83, 84 and four lower electromagnets 85, 86, 87, 88. (In all, there will be sixteen electromagnets, as two scales are presumed for the illustrated embodiment.) The sensor 53 is connected as an input to the microprocessor 72 to inform the microprocessor whether the scale is retracted or deployed. The sensor 53 makes such a determination by noting the presence or absence of contact upon it by the lower structural piece. When the lower structural piece is in its retracted position, it bears on the sensor. Noting this, the sensor informs the microprocessor that the scale is in its retracted position. When no contact is bearing on the sensor 53, it correspondingly informs the microprocessor that the scale is in its deployed position. By this means the microprocessor employs the appropriate four electromagnets in order to bring about the inward withdrawal of the appropriate four cam locks each time the push button 19 is utilized. More fully, to deploy the scale from its retracted position, the lower four electromagnets 85, 86, 87, 88 are utilized to withdraw inwardly the lower four cam locks. At this point, the large spring acts to impel the lower structural piece downward causing it to project approximately 3/16" beneath the ground line of the shoe.

To allow the scale to be retracted from its deployed position, the upper four electromagnets 81, 82, 83, 84 are utilized to withdraw the upper four cam locks. With these four locks thus released, the wearer will bring about the retraction of the scale by placing their weight upon the now extended scale in order to cause its upward travel. By means of the concavity associated with the scale, the wearer will complete the secure seating of the scale, now fully raised and locked in its retracted position. This concavity allows the wearer to seat the scale so that the scale's lowest point, when fully and securely seated, is approximately 3/8" above the shoe's ground line. To utilize the concavity in order to fully seat one of the scales, the wearer may, for instance, utilize a corner of the horizontal surface of a porch stair. It should further be noted that when the lower electromagnets are utilized, it is for a brief time only. The large spring deploys the lower structural piece immediately upon the release of the lower cam locks, causing a need for the according electromagnets to be in use—activated—for a very short time only. However, when the upper cam locks are released, allowing the lower structural piece to be retracted, the electromagnets are activated for a longer period of time. This consideration thereby provides a reasonable time for the wearer to bring about the retraction of the lower structural piece. These differing allotments of time are, of course, achieved by means of the sensor, the microprocessor, and the electromagnets functioning as parts of the electronic circuit.

It should be noted that the strain gage is electronically active only when the lower structural piece is not in contact with the sensor. It should also be noted that if multiple scales are used in conjunction with the invention, they would communicate by means of the electronic circuitry.

The operation, to the extent not described above, is straightforward; i.e., the wearer of the shoe, when a weight measurement is desired, pushes the push button. This brings about the deployment of the scales. The wearer then stands on one foot—that with the shoe containing the scale—until the tone signaling the capture of all accurate weight determination is heard. To retract the scale, so as to make possible the further use of the shoe for conventional purposes, the wearer again pushes the push button. The scale may then be retracted—either by the wearer's weight being exerted upon it as she stands upon it, or manually, by the wearer's pressing of the scale back up into the shoe using the fingers of one or both hands. All of these functions are aided by the electronic circuit.

It will be understood that while one illustrative mechanism is herein disclosed, the invention may be implemented in various ways and that the description herein essentially is of only one embodiment and implementation. For example, as to the means by which the shoe's various functions may be powered, in addition to the battery means herein described, the power source utilized may be a mechanical means (the force of the wearer's weight applied to the deployed scale—seating it within the shoe—being used to produce and store energy; the force of the wearer's pushing of the push button used in a like fashion); or a means that uses electrical power that includes a solenoid; or a combination of electrical and mechanical power; or hydraulic power—perhaps in combination with electrical power; or pneumatic power—perhaps in combination with electrical power; or small but conventional electrical generators; or a piezoelectric-powered system. It may also be desirable to use the present invention in combination with "energy harvesters"—personally-powered bodily-mounted electrical generators. These devices produce low levels of electrical energy that could be transmitted through wires to the shoe.

The invention may also be implemented using strain gages housed in several alternative positions from those suggested in the drawings above. As an example, strain gages may be housed in the shoe's tread material in an implementation of the invention wherein the deployable and retractable scales have as their lowest, ground-engaging surface, appropriately-sized segments of the sole itself. In this version, when the scales are not deployed, the bottom of the tread-covered scales are even with the remainder of the shoe's sole. Also, in this implementation, when the scales are not deployed, electrical power to the strain gages is interrupted.

Also, strain gages are not the only means by which accurate weight information could be determined for purposes of this invention's implementation: piezoelectric devices, Hall-effect devices, conventional spring scales, extensometers, accelerometers, manometers, Sperrymeters, dielectric elastomers, magnetic sensors that measure compression, and certain transducers not here mentioned—but well known to those skilled in the art—might also be used.

The implementation of the invention may also include the means by which its weight determination will contain an allowance for the predetermined weight of the wearer's garments, including that portion of the one shoe's weight that falls above the strain gage—when the scale is deployed—as well as the other, non scale-equipped shoe. Thereby, an individual's true weight may be accurately stated. (One's weight, obtained with one or more strain gages and a microprocessor, can be very accurately calibrated and presented, virtually instantly, in pounds and ounces—or pounds and tenths of pounds.)

The invention herein described may be implemented by employing any or all of these materials in its construction: polymer, polycarbonate, fiber glass, steel, aluminum, or titanium. Other suitable materials, including those utilizing carbon fiber technology, may also be utilized.

The implemented invention may also include flexible gaskets, made of sole-like material, that help to seal the apertures on the bottom of the sole through which the scale's lowest portion is deployed and retracted. The invention's implementation may include a means whereby the scale itself may be removed from its position within the shoe's sole for purposes of cleaning. After cleaning, it would be reinserted in the shoe's sole for continued use.

In addition, a variety of locking mechanisms not described in the above drawings may be used in the invention's implementation, including those that would be manually operated. Folding, knee-type mechanisms may also be used to deploy the scales in the invention; the scales may also be deployed with scissor-type mechanisms similar to those used to deploy wheels on skate shoes and the like; the scales could also be deployed by means of telescopic, spring-loaded pillars at each of the scale's four corners.

Additionally, the invention may be implemented in many types of shoe, boot, or sandal.

What is claimed is:

1. A shoe with at least one scale retractably mounted in the sole comprising:
   a shoe with a permanently attached sole having a bottom ground engaging surface;
   a scale permanently attached to the sole but selectively movable between a retracted position and a deployed position;
   a cavity in the sole to receive the scale in the retracted position;
   a lower set of locks to hold the scale in the retracted position;
   an upper set of locks to hold the scale in the deployed position wherein it extends partly below the bottom surface;
   bias means to urge the scale in the direction of the deployed position;
   a device for selectively activating the lower and upper sets of locks; and
   a display operatively connected to the scale to produce a visual indication of the weight of the wearer of the shoe.

2. A shoe as described in claim 1 wherein the scale includes a strain gage.

3. A shoe as described in claim 1 further including a microprocessor connected between the scale and the display.

4. A shoe as described in claim 1 further including a radio-frequency telemetry device electronically connected for use in the remote display of weight data produced by the scale.

5. A shoe as described in claim 4 further including a microprocessor connected between the scale and the radio-frequency telemetry device.

6. A shoe as described in claim 1 further including a sound and/or speech-simulation device electronically connected to announce weight data produced by the scale.

7. A shoe as described in claim 6 further including a microprocessor connected between the scale and the sound and/or speech-simulation device.

8. A shoe as described in claim 1 further including electromagnets to activate said locks.

9. A weight-measuring shoe comprising:
   a shoe with a permanently attached sole;
   a scale mounted within the sole and moveable between a retracted position and a deployed position;
   a structural mechanism for selectively moving the scale between the retracted position and the deployed position; and
   electronic circuitry connected to the scale for producing a reading of the weight of the person wearing the shoe.

10. A shoe as described in claim 9 further including an information-display device, affixed to the shoe and operatively connected to the scale by means of the electronic circuit, for displaying weight data derived when the scale is in the deployed position.

11. A shoe as described in claim 9 further including a radio-frequency telemetry device, operatively connected to the scale by means of the electronic circuit, for use in the remote display of weight data derived when the scale is in the deployed position.

12. A shoe as described in claim 9 further including a sound and/or speech-simulation device, operatively connected to the scale by means of the electronic circuit, for announcing weight data derived when the scale is in the deployed position.

* * * * *